United States Patent [19]
Wen et al.

[11] Patent Number: 5,690,637
[45] Date of Patent: Nov. 25, 1997

[54] GUIDE FOR PATELLAR CUTS

[75] Inventors: Ning Wen, Chantilly; Rémy Charpenet, Epinal; Henri Coudane, Nancy Cedex; Jean-Luc Roure, Paris; Christian Dongar, Viarmes; Jean-Claude Junger, Vandoeuvre Les Nancy, all of France

[73] Assignee: France Bloc, Viarmes, France

[21] Appl. No.: 631,340

[22] Filed: Apr. 12, 1996

[30]  Foreign Application Priority Data

Apr. 13, 1995  [FR]  France ................... 95 04465

[51] Int. Cl.$^6$ ........................................... A61B 17/15
[52] U.S. Cl. ........................ 606/88; 606/82; 606/89; 606/87; 606/86
[58] Field of Search ........................ 606/86–88, 96, 606/82, 79

[56] References Cited

U.S. PATENT DOCUMENTS 4,565,192  1/1986  Shapiro .
5,108,401  4/1992  Insall et al. .

FOREIGN PATENT DOCUMENTS

8909290 U  2/1989  Germany .
0 575 232 A1  6/1992  Germany .

*Primary Examiner*—Michael Buiz
*Assistant Examiner*—Daphna Shai
*Attorney, Agent, or Firm*—Browdy and Neimark

[57]  ABSTRACT

Guide which allows a precise patellar cut to be made for fitting the prosthetic patella of a knee prosthesis using a trial femoral component, having a sliding plate (20) of a pin guide (30), a pin guide (30) comprising at least two channels (33) for guiding pins (50), which are installed perpendicularly to the sagittal plane of the condyle, and comprising two panels having two surfaces (32, 34) arranged at a right angle, the first panel having a flat surface (32) and a central aperture (31), and the second panel having a flat surface (34) towards the inside of the guide, a securing element (40) which cooperates with the shaft (23) to lock the pin guide (30) with respect to the sliding plate (20) and thus avoid translation movements.

8 Claims, 2 Drawing Sheets

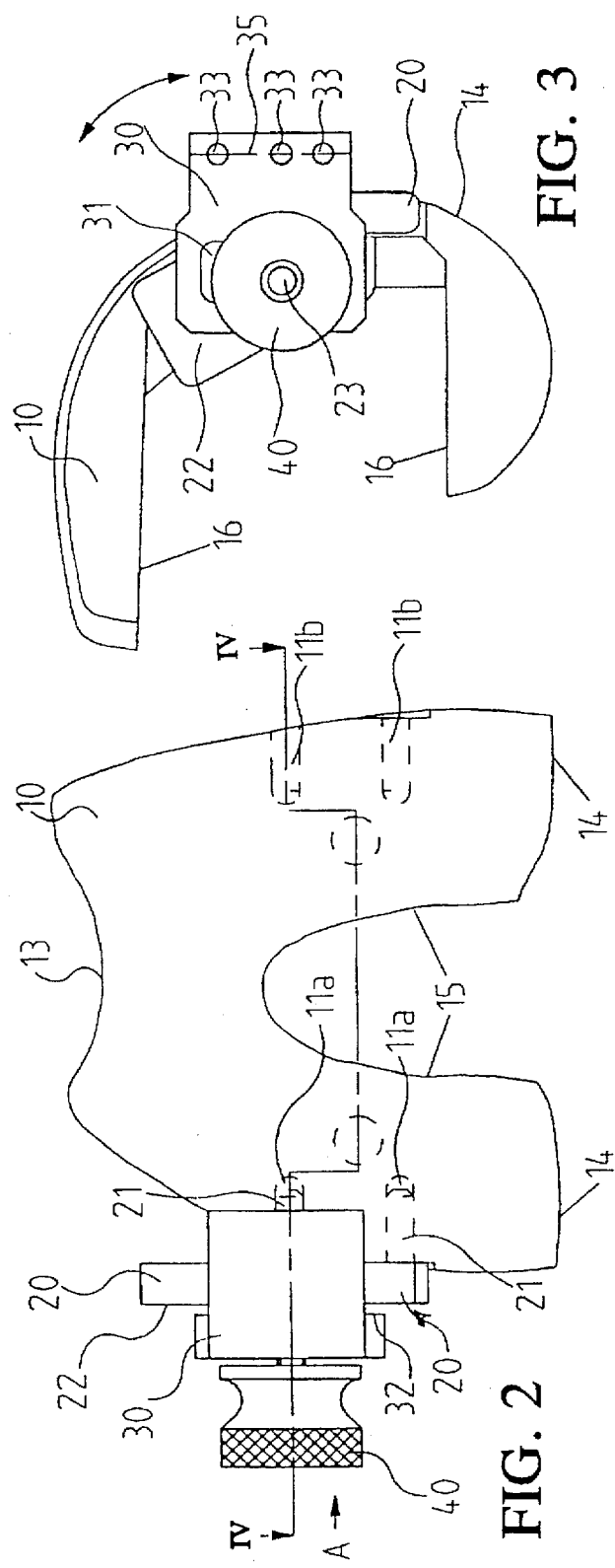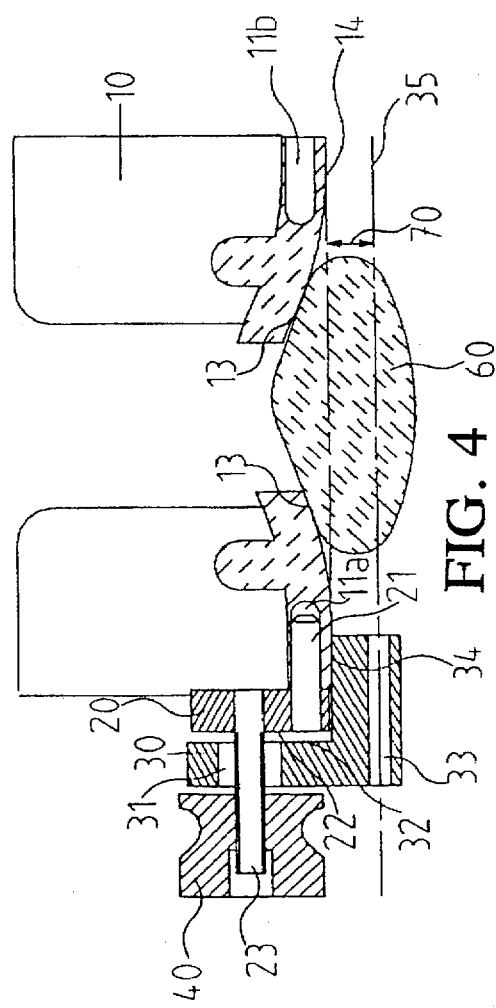

GUIDE FOR PATELLAR CUTS

The present invention relates to a guide which allows a precise patellar cut to be made for fitting the prosthetic patella of a knee prosthesis.

The field of use of the invention is in the fitting of the prosthetic patella of a tri-compartmental knee prosthesis. It is noted that the prosthesis is made up of three components:

- the femoral component
- the tibial component
- the patellar component

Positioning of the prosthetic patella is often the last stage in fitting a knee prosthesis.

To achieve this, it is necessary to remove a thickness of bone of the anatomical patella including the articular surface. This will be replaced by a prosthetic patella having the same thickness as that of the bone removed.

Proper functioning of a knee prosthesis can be achieved only if the isometry and the tension of the ligaments are maintained; this can only be done by making cuts of precise thickness and orientation for implantation of the prosthetic elements.

To make the patellar cut it is necessary to turn out the anatomical patella in order to render the articular surface visible. This will be held with the aid of forceps, the jaws of which will serve as the cutting plane in order to make the patellar cut. The forceps are positioned visually, attempting to achieve uniform division of the bone. The cut made in this way may be angled and results in poor positioning of the patellar implant, which will have a tendency to dislocate.

The thickness of the patellar cut is currently determined by taking the crest of the anatomical patella as a reference. Since the anatomical patella is often worn, this anatomical crest is also worn and therefore cannot be a good reference for the cut. The cuts made in this way are sometimes too thin, which results in a raised prosthetic patella and a limit to flexion, or too thick, which renders the anatomical patella delicate and may cause fractures.

There is also another method which defines the cutting plane of the anatomical patella with respect to the trochlea of the femoral component. This method requires the knee to be bent at a fixed angle, a flexion at which the anatomical patella is engaged in the groove of the trial femoral component. It is assumed that the anatomical patella is perfectly stable in the prosthetic trochlea. By taking a reference on the femoral component, the patellar cut can be made, which will enable the patellar component to be placed without disturbing the kinematics of the knee.

Unfortunately, the trochlea of the femoral component does not have a complementary shape like the anatomical trochlea; it is much less hollow, which allows the anatomical patella to rock in the prosthetic trochlea and cause a error in the positioning (orientation and thickness) of the patellar component.

The aim of the present invention is to propose a guide for patellar cuts for positioning the patellar component during fitting of a tri-compartmental prosthesis of the knee joint. This guide allows a patellar cut to be made, achieving a good thickness of the cut and good orientation of the plane of the cut.

To make a correct patellar cut, it is necessary to have a stable and precise reference. This obviously means that the anatomical patella should be stable.

The guide for patellar cuts according to the present invention is mounted on the trial femoral component by placing, for example, two lugs of the cut guide into two complementary cylindrical holes made on the sides of the trial femoral component. The guide for the cuts is thus positioned with respect to the trial femoral component.

The cut guide according to the invention is broken down into a sliding plate which defines a plane strictly perpendicular to the bone cuts of the femoral condyle (cuts made for fitting the femoral component), a pin guide which can both effect translation and pivot on the above plate in order to be placed both in the plane of the anatomical patella, outlined in a profile view by a line drawn between the insertion of the quadricipital tendon and that of the patellar ligament, and to be in contact with the articular surface (profile form) of the trial femoral component, and a securing element, such as a nut which cooperates with a thread allowing the relative position between the various above-mentioned pieces to be locked. The orientation and thickness of the cut is thus defined by taking the articular surface of the trial femoral component as a reference. The pin guide preferably has more than 2 guiding channels, advantageously cylindrical, which enable nails which serve to assist in the guiding operation for making the patellar cut to be fixed in the anatomical patella.

The present invention thus relates to a guide which allows a precise patellar cut to be made for fitting the prosthetic patella of a knee prosthesis using a trial femoral component, characterized in that it comprises:

i) a sliding plate of a pin guide, the said plate having, on the side opposite to the trial femoral component, a flat sliding surface parallel to the sagittal plane of the condyle of the trial femoral component, and a shaft installed perpendicularly to this sliding surface, and having, on the side of the trial femoral component, at least one protuberance of complementary shape to a recess provided in the trial femoral component in order to be fixed thereto, a plate on which slides ii) a pin guide comprising at least two channels for guiding pins, installed perpendicularly to the sagittal plane of the condyle, and comprising two panels having two surfaces arranged at a right angle, the first panel, parallel to the sagittal plane, having
- a flat surface parallel to the sagittal plane which can slide in contact with the sliding surface of the plate
- a central aperture allowing passage of the shaft through the first panel, of dimensions sufficient to allow translation of the pin guide in all directions parallel to the sagittal plane the second panel, perpendicular to the first panel, situated on the side of the trial femoral component, having, towards the inside of the guide, a flat surface of dimensions sufficient to come into contact with the articular surface of a trial femoral prosthesis during the translation movements of the pin guide, and also comprising channels for guiding pins, iii) a securing element which cooperates with the shaft to lock the pin guide with respect to the sliding plate and thus to avoid translation movements.

The essential elements of the sliding plate are its flat sliding surface, the shaft which limits displacements of the sliding plate and is used to lock the pin guide, and the protuberance which cooperates with the trial femoral component in order to be fixed thereto.

The shaft installed perpendicularly to the sliding surface is advantageously a threaded shaft; it thus constitutes a simple means which can cooperate with a corresponding threaded nut to lock the pin guide with respect to the sliding plate and thus avoid translation movements of the latter. Any other means which allows the pin guide to be secured against the sliding plate, such as a lever system or an eccentric system, can of course be used.

The protuberance which is situated on the sliding plate and allows fixing of this to the trial femoral component is, for example, a parallelepipedal element. It can also be a shaft of hexagonal or square section, for example. In preferred embodiments, and as illustrated on the figures, it is two studs or tappets which can be inserted with gentle friction into two lateral orifices provided, for example, on each of the condyles of the trial femoral component.

The essential function of the pin guide is to be able to slide parallel to the sagittal plane of the condyle of the trial femoral component due to a flat surface parallel to this sagittal plane.

This flat surface situated on a first panel comprises an aperture which allows passage of the shaft through the first panel.

In order to allow translation of the pin guide in all directions parallel to the sagittal plane, this aperture is advantageously extended in the direction corresponding to displacement of this component according to the femoral articular surface. Its width will advantageously be at least one and a half times, and preferably twice, the width of the shaft situated on the sliding plate. This aperture in the sliding surface will have, for example, as illustrated on the drawings, a rectangular shape, preferably with rounded angles.

As can be seen by those skilled in the art, the shape of the surface of the first panel opposite to the flat surface which can slide in contact with the sliding surface of the plate is not critical. However, this surface is advantageously flat and parallel to the said surface which can slide in contact with the sliding surface of the plate. Easy locking of the pin guide can thus be achieved by using a screw situated on the sliding plate and an adjusting and locking nut.

The essential element of the second panel of the pin guide is its flat surface of dimensions sufficient to come into contact with the articular surface of a trial femoral prosthesis. As a result, the surface of this panel opposite to the surface which comes into contact with the articular surface can have any shape. For practical production reasons, this surface will advantageously be parallel to the abovementioned surface.

In preferred embodiments, the pin guide thus has roughly the shape of two flattened right-angled parallelepipeds installed perpendicularly with respect to one another and of general L-shaped cross-section. The channels of the pin guide also pass through this second panel. These channels are thus installed perpendicularly to the sliding surface of the sliding plate and perpendicularly to the first panel of the pin guide. These channels are at least two in number, and are advantageously three or four in number, preferably three in number.

The description which follows, taking into account the attached drawings, which are given by way of illustration, will explain what the invention comprises and how it can be implemented and used.

FIG. 2 is a front view of the same guide.

FIG. 3 is a side view according to A, referring to the front view of FIG. 2.

FIG. 4 represents the section along IV—IV of the component in front view.

Figure 1:
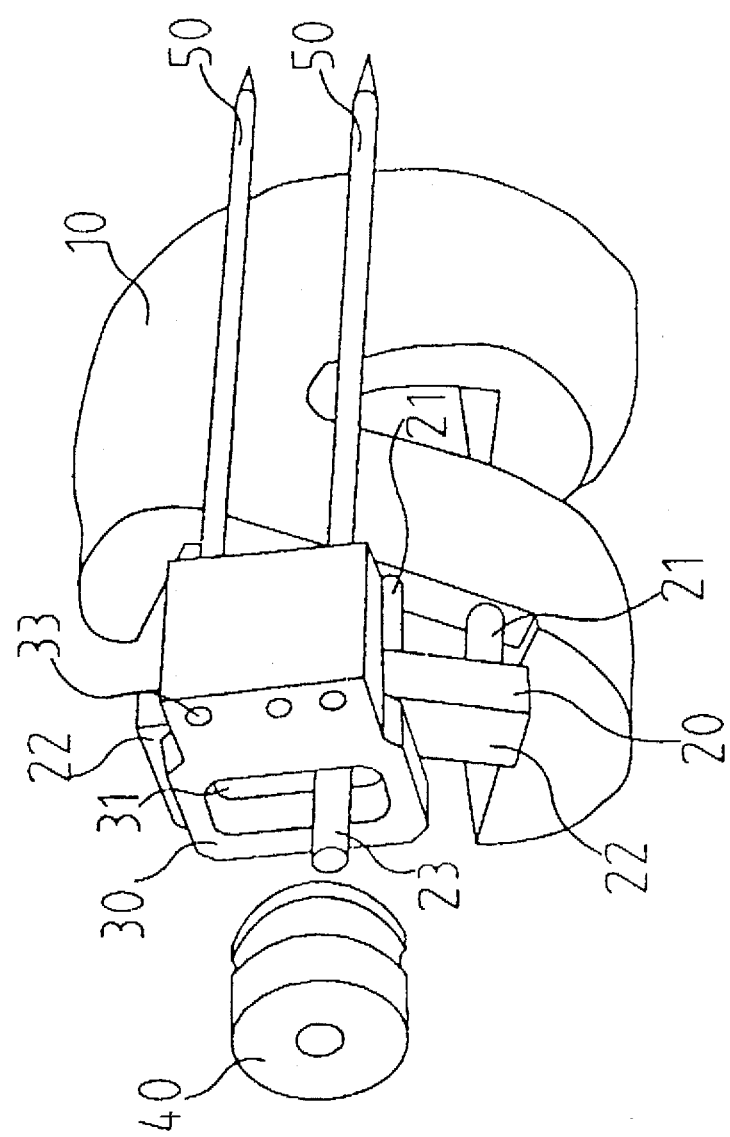
FIG. 1 is a perspective view of the guide for patellar cuts mounted on the trial femoral component.

With reference to these drawings, the device comprises, on the one hand, a trial femoral component 10 of the type having the same shape as the definitive femoral component, and, on the other hand, an ancillary guide for patellar cuts comprising four parts, a sliding plate 20 fixed on the trial femoral component 10, a pin guide 30 sliding on the plate 20, an adjusting screw 40 which allows the position of the pin guide 30 with respect to the plate 20 to be locked, and pins 50 of standard diameter which are provided for implantation into the anatomical patella 60, and are guided by the three tubular channels of the pin guide 30, and as a reference for the patellar cut.

The trial femoral component 10 of the type described is symbolically composed of a groove of the trochlea 13 descending from the supero-anterior part to the antero-distal part (at this point the groove of the trochlea 13 is cut by the intercondylar channel 15), on which the anatomical patella 60 or the prosthetic patella slides, of a flattened articular surface 14, of bone cutting planes 16 and of two cylindrical holes 11a or 11b, the axis of which is parallel to the bone cutting planes 16 and perpendicular to the plane of the profile of the trial femoral component, both on the inside and on the outside. In fact, to install a total knee prosthesis, during the operation the knee joint is preferably accessed from the inside; the two holes 11 situated on the inside of the condyle of the trial femoral component used are thus utilized. Access to the knee joint by the external route is rare.

When the knee is bent severely, the anatomical patella 60 is above the channel 15 and its crest no longer touches the base of the trochlea 13.

The sliding plate 20 is composed essentially of two protuberances in the form of cylindrical studs 21 which enter into the two lateral cylindrical holes 11a or 11b in the trial femoral condyle of corresponding size, of a sliding surface 22 perpendicular to the lateral holes 11a, 11b or to the bone cutting planes 16 of the trial femoral component, and of a threaded shaft 23.

The pin guide 30 is a component of right-angled "L"-shaped cross-section having a sliding surface 32 which slides on the sliding surface 22 of the plate. It is made up of two essentially parallelepipedal panels which are perpendicular to one another, of "L"-shaped cross-section. The first panel which slides on the plate 20 comprises an aperture 31, the width of which is greater than the diameter of the threaded shaft 23, allowing both good mobility of the pin guide 30 with respect to the sliding plate 20, while limiting displacement. The second panel comprises several tubular channels 33 to guide the pins 50, of which the axis 35 of the pins 50 or the tubular channels 33 is perpendicular to the plane of the profile of the trial femoral component. The second panel also comprises a flat contact surface 34 which is intended to be brought into tangential contact with the articular surface 14 of the trial femoral component. With such an arrangement, a known cut thickness 70 with respect to the trial femoral component is obtained.

The adjusting screw 40 allows, after correct positioning of the pin guide 30, locking of this before fitting of the pins 50 in the anatomical patella 60.

Since the distance 70 between the flattened articular surface 14 and the axis 35 of the pin 50 is known, the thickness of the patellar Cut can thus be regulated with respect to the articular surface 14 of the trial femoral component 10.

The guide according to the invention is intended for making a patellar cut of precise thickness and orientation and as a result occupies a position as one of the ancillaries of a knee prosthesis.

We claim:

1. A guide which allows a precise patellar cut to be made for fitting a prosthetic patella of a knee prosthesis using a trial femoral component, the trial femoral component including an articular surface (14) and having a sagittal plane of the condyle;

(i) a sliding plate (20), the plate including, on a side opposite to the trial femoral component, a flat sliding surface (22) parallel to the sagittal plane of the condyle of the trial femoral component, and a shaft (23) installed perpendicularly to the sliding surface (22), and including, on a side adjacent the trial femoral component, at least one protuberance (21) of a complementary shape to a recess (11a) provided in the trial femoral component comprising means to be fixed thereto;

(ii) a pin guide (30) comprising at least two channels (33) for guiding pins (50), installed perpendicularly to the sagittal plane of the condyle, and an L-shaped piece comprising two panels including a first panel and a second panel having two respective flat surfaces (32, 34) forming a right angle therebetween;

the first panel, parallel to the sagittal plane, having the first flat surface (32) parallel to the sagittal plane comprising means to slide in contact with the sliding surface (22) of the plate (20);

a central aperture (31) comprising means for passage of the shaft (23) through the first panel, the aperture being of dimensions sufficient to allow translation movements of the pin guide (30) in all directions parallel to the sagittal plane;

the second panel, perpendicular to the first panel, situated on the side of the trial femoral component, having, towards the inside of the guide, having the second flat surface (34) of dimensions sufficient to come into contact with the articular surface (14) of the trial femoral component during the translation movements of the pin guide (30), and also comprising channels (33) for guiding pins (50);

(iii) a securing element (40) comprising means to cooperate with the shaft (23) to lock the pin guide (30) with respect to the sliding plate (20) and thus to avoid the translation movements.

2. Guide according to claim 1, characterized in that the shaft (23) is threaded, and the securing element (40) is of the nut type.

3. Guide according to claim 2, characterized in that the sliding plate (20) comprises two protuberances (21) in the form of elongated studs.

4. Assembly for a patellar cut comprising a guide as defined in claim 3, and a trial femoral component comprising recess (11a, 11b) of complementary shape provided in at least one of the condyles of the trial femoral component.

5. Assembly for a patellar cut comprising a guide as defined in claim 2, and a trial femoral component comprising recess (11a, 11b) of complementary shape provided in at least one of the condyles of the trial femoral component.

6. Guide according to claim 1, characterized in that the sliding plate (20) comprises two protuberances (21) in the form of elongated studs.

7. Assembly for a patellar cut comprising a guide as defined in claim 6, and a trial femoral component comprising recess (11a, 11b) of complementary shape provided in at least one of the condyles of the trial femoral component.

8. Assembly for a patellar cut comprising a guide as defined in claim 1 and a trial femoral component comprising a recess (11a, 11b) of complementary shape provided in at least one of the condyles of the trial femoral component.

* * * * *